(12) United States Patent
Scarcello

(10) Patent No.: US 7,985,233 B2
(45) Date of Patent: Jul. 26, 2011

(54) DEVICE FOR ANASTOMOSING ANATOMICAL DUCTS

(75) Inventor: Edoardo Scarcello, Empoli (IT)

(73) Assignee: Giuseppe Triggiani, Pisa (IT)

( * ) Notice: Subject to any disclaimer, the term of this patent is extended or adjusted under 35 U.S.C. 154(b) by 1702 days.

(21) Appl. No.: 10/485,244

(22) PCT Filed: Jul. 30, 2002

(86) PCT No.: PCT/IB02/02952
§ 371 (c)(1),
(2), (4) Date: May 7, 2004

(87) PCT Pub. No.: WO03/011182
PCT Pub. Date: Feb. 13, 2003

(65) Prior Publication Data
US 2004/0186548 A1 Sep. 23, 2004

(30) Foreign Application Priority Data

Aug. 1, 2001 (IT) .................................. PI2001A0055
Jan. 16, 2002 (IT) .................................. PI2002A0005

(51) Int. Cl.
*A61B 17/08* (2006.01)
(52) U.S. Cl. ........ 606/153; 606/155; 606/213; 606/215; 623/1.11

(58) Field of Classification Search .................. 606/153, 606/155, 213, 215; 623/1.11, 1.15, 1.23
See application file for complete search history.

(56) References Cited

U.S. PATENT DOCUMENTS 5,449,382 A * 9/1995 Dayton .................. 623/1.15
6,743,243 B1 * 6/2004 Roy et al. .................. 606/153

* cited by examiner

*Primary Examiner* — Vy Q Bui
(74) *Attorney, Agent, or Firm* — Simpson & Simpson, PLLC

(57) ABSTRACT

A medical device for treatment of affection of anatomical ducts, as in particular for anastomosing blood vessels and vascular prosthesis, with end-to-end or end-to-side configuration. The device has outer containing functions and is associated to an intra-prosthetic stent for sandwiching the overlapping segments being anastomosed to each other of the anatomical ducts and of the prosthesis, a segment of which is located in the duct. The outer containing device is formed by a stent of biocompatibile resilient material having memory effect, in a predetermined nominal position, suitable for extending elastically for engaging the outside of the duct, and returning to said nominal position, with containing function, thus preventing the diameter of the duct from increasing and without compressing the duct. The stent must have at least a length not less than half the outside diameter of the duct. Means are provided for putting the prosthesis in the duct and for arranging the containing device out of the duct.

9 Claims, 15 Drawing Sheets

Fig. 3
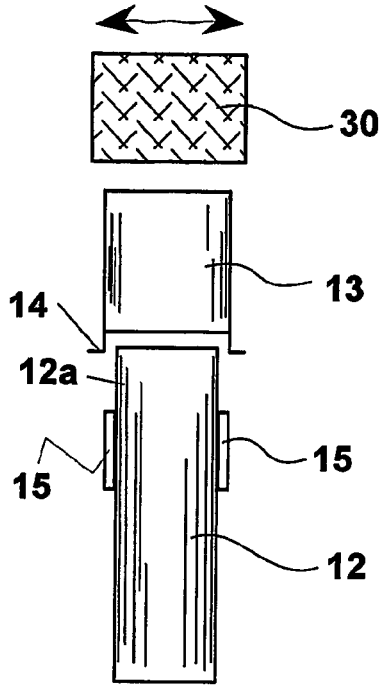
Fig. 3A
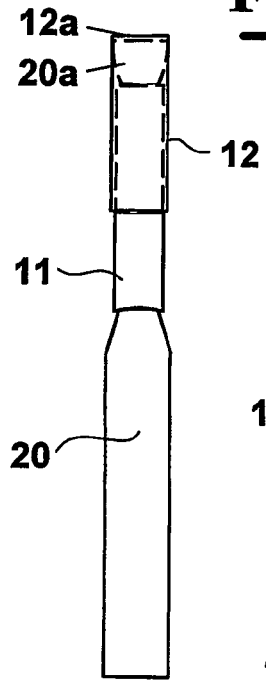
Fig. 3B
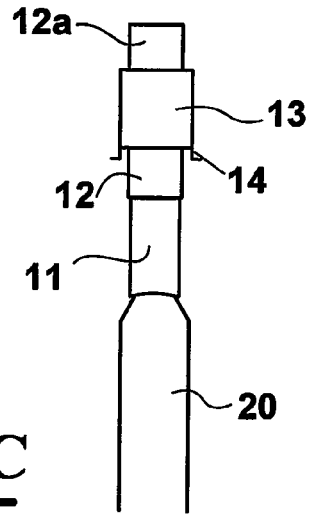
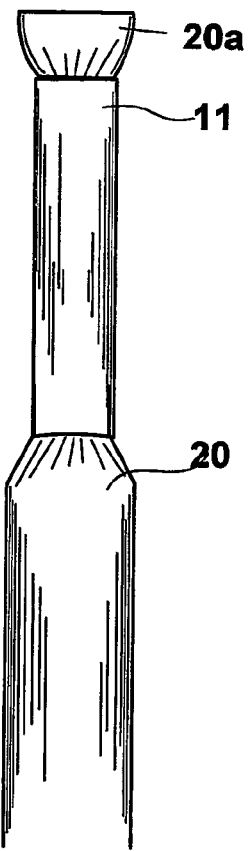
Fig. 3C
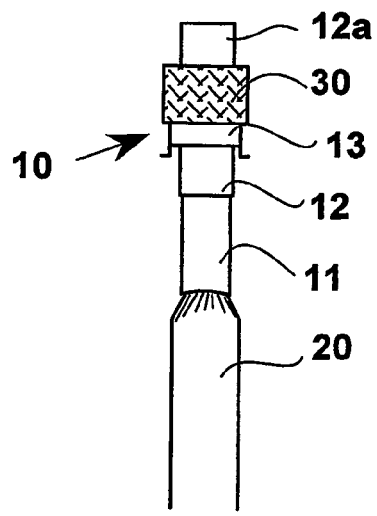

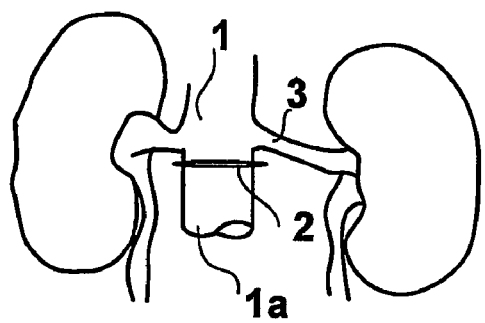
Fig. 4
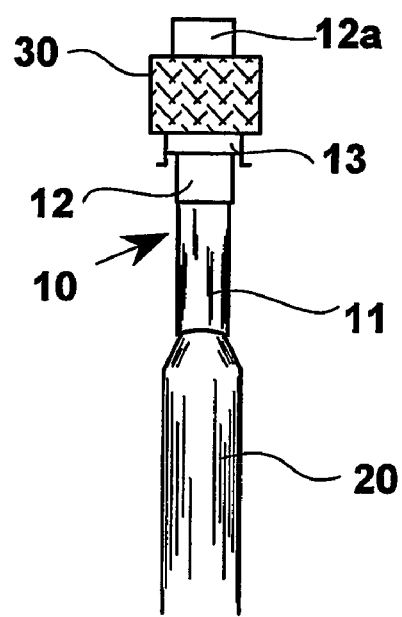
Fig. 5
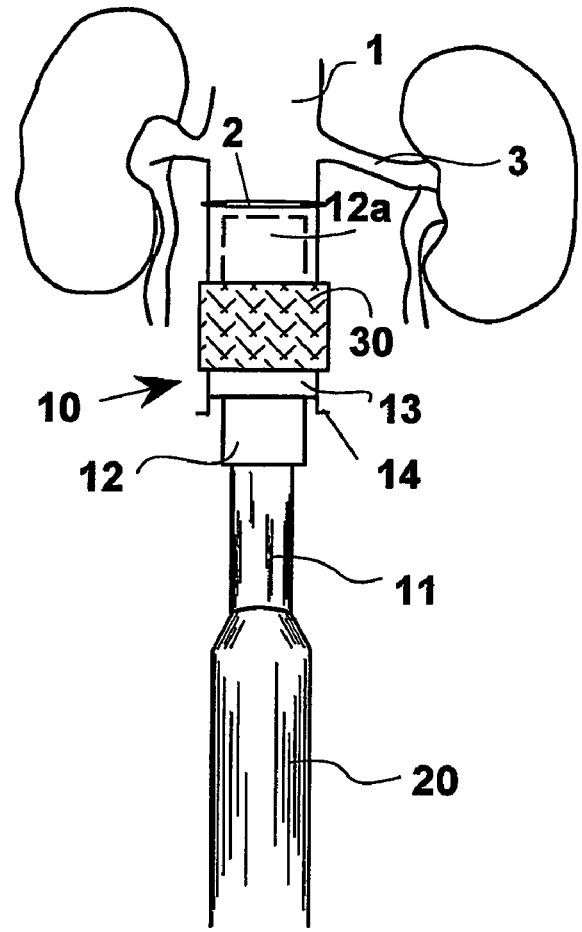

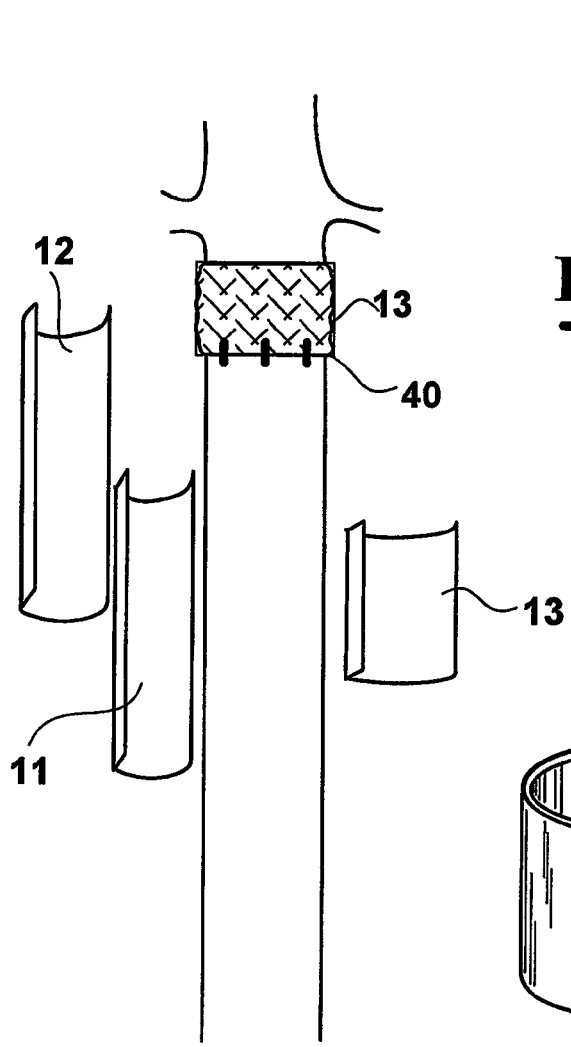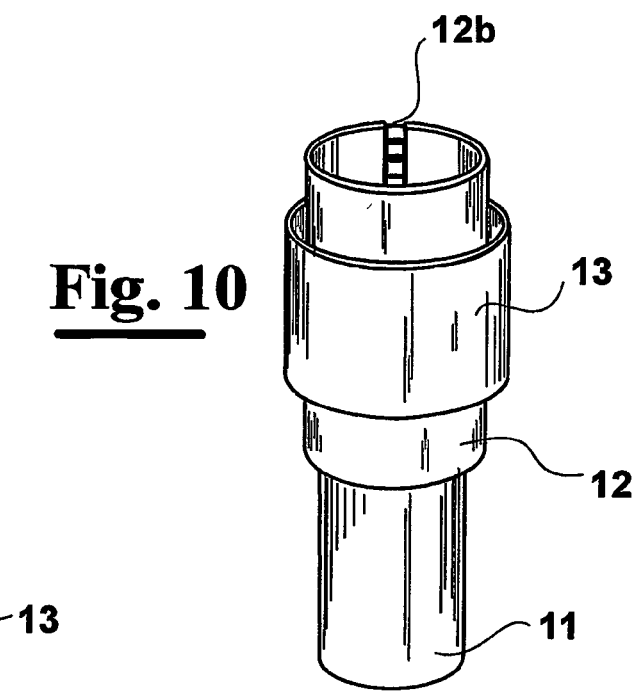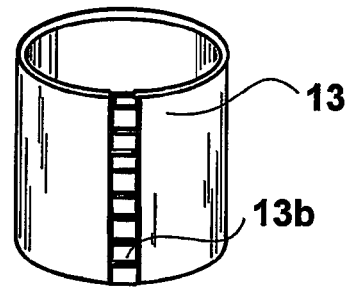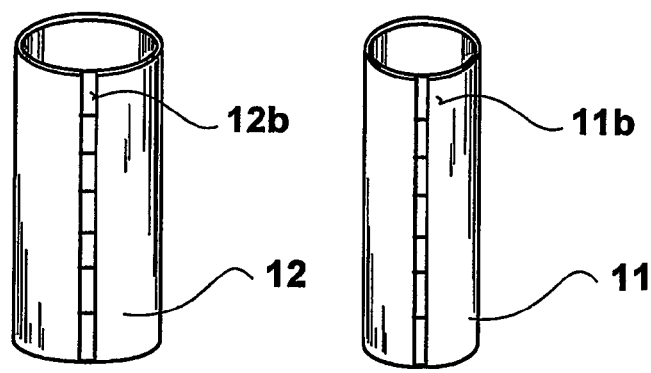

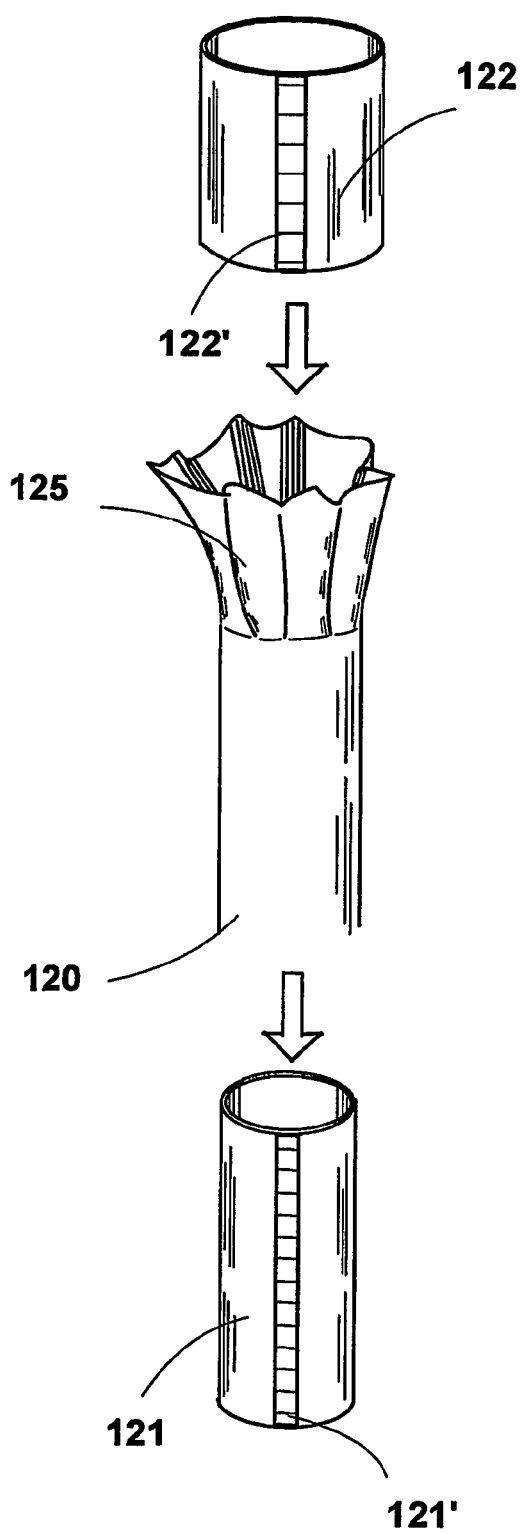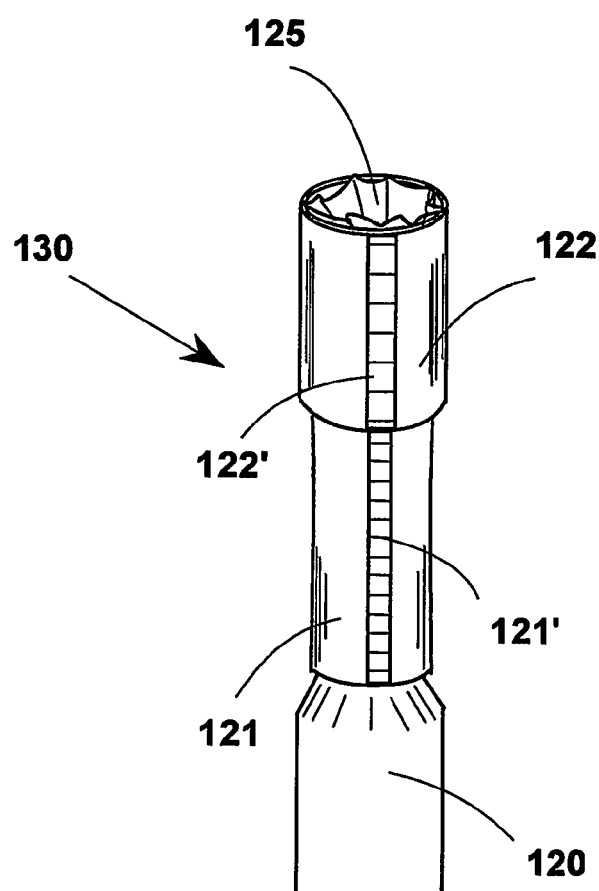

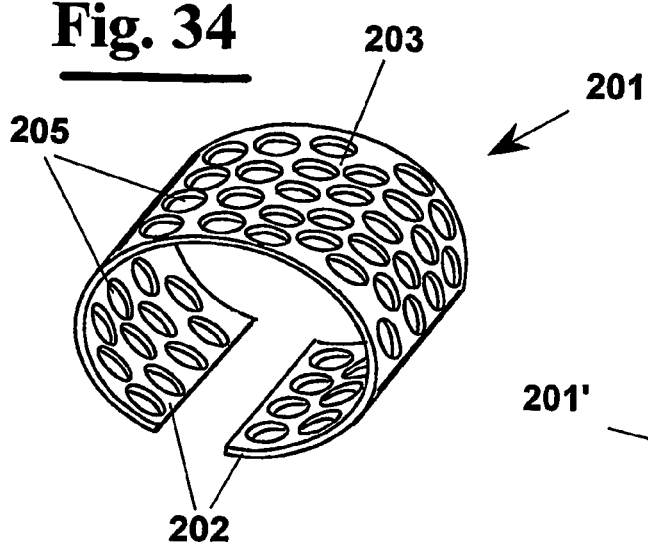
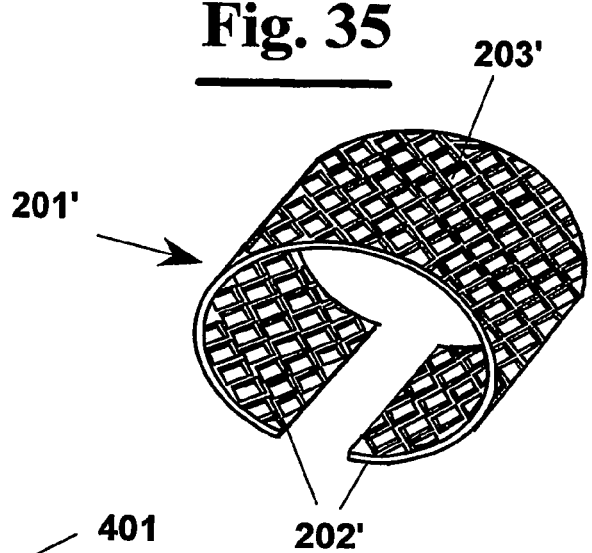
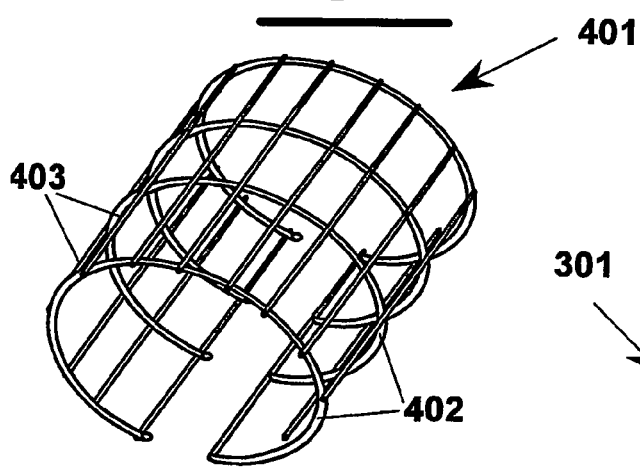
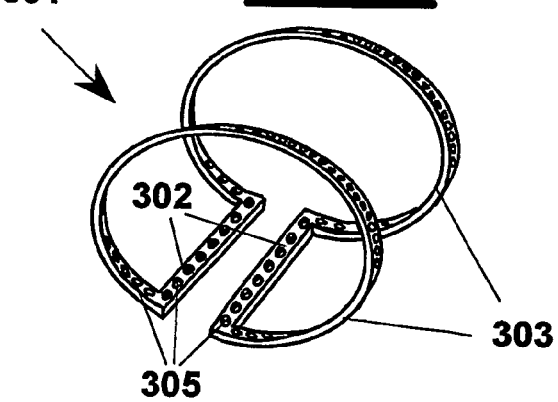
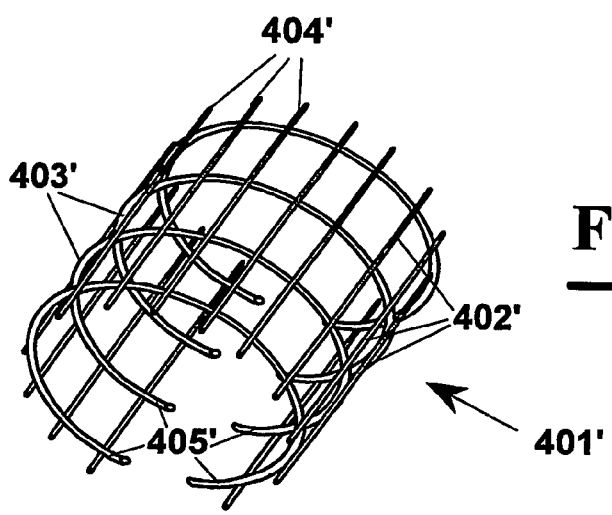

DEVICE FOR ANASTOMOSING ANATOMICAL DUCTS

CROSS REFERENCE TO RELATED APPLICATIONS

The present application is the U.S. national stage application pursuant to 35 U.S.C. §371 of International Application No. PCT/IB02/12952, filed Jul. 30, 2002, which application claims benefit of Italian Application No. PI2002A000005, filed Jan. 16, 2002, which application claims benefit of Italian Patent Application No. PI2001A000055, filed Aug. 1, 2001.

FIELD OF THE INVENTION

The present invention relates to medical devices useful for treatment of affection of anatomical ducts, which, owing to stenosing or ectatic pathology, requires the reinstatement of a correct canalisation.

In particular, without any limitation to the extent of the invention, the device relates to anastomosis between blood vessels and vascular prosthesis, either synthetic or biological, with end-to-end or end-to-side configuration.

DESCRIPTION OF THE PRIOR ART

Presently two main methods are known for making an anastomosis:
- applying hand-sewn anastomosis, running sutures or multiple separate stitches, for fixing two structures to each other;
- applying stent-grafts, typical of endoluminal aortic aneurysm repair, where expanding stents provide radial support that promote fixation, sometimes with hooks or barbs.

These two methods are associated to modern procedures and devices for making the anastomosis easier and if possible automatic.

An automatic anastomosis with circumferential suture with separate stitches can be made, for example, with a device called "Heartflo" (Perclose/Abbott Labs, Redwood City, Calif.). This device allows automatic end-to-end and end-to-side anastomosis of vessels, via a simultaneous delivery of separate stitches, during coronary artery bypass graft (CABG) surgery.

On the other hand, examples of devices for anastomosing without separate stitches or running suture are the following:
A) a device called "GraftConnector" (Jomed Innertional, Helsingborg, Sweden). This device is a T-shaped polytetrafluoroethylene (ePTFE) connector with a self-expanding stent inside. This device allows sutureless anastomosis through: 1) after arteriotomy, insertion into the artery of a prosthesis horizontal section; 2) connection of the other vessel or prosthesis in a vertical branch. This device has been applied in the verification of utility and safety of use in cardiac surgery.
B) a device called "AAD"—Aortic Anastomotic Device (Bypass Ltd, Herzelia, Israel). It is a extra-vessel autoexpansible device of Nitinol. Consists of a central cylindrical body formed by elliptical interconnected arcs and two sets of five pointed ends, opposite to each other. The juxtaposition of the two sets causes the vessel and the prosthesis to be integral to each other, thus obtaining the anastomosis.
C) a device for end-to-side anastomosis between saphenous vein and coronary artery developed by St. Jude Medical Anastomotic Technology Group (Minneapolis, Minn., USA). It consists of a metal device, expansible with balloon, put in place by means of a special instrument. This connector has a double set of pointed ends, which, once located and expanded the device, allow the vessel and the prosthesis to be integral to each other, thus obtaining the anastomosis.

A further approach, described in US20010037137A1, valid for end-to-side anastomosis, provides the intra-vascular introduction in a main artery of a stent with a side opening, in which always intra-vascularly a side prosthesis is put, having in the proximal end an radial abutment, suitable to fit with the inner edges of the opening.

Finally in U.S. Pat. No. 6,248,116 an outer reinforced thin belt-shaped application device is described of stent grafts that supports separate stitches.

SUMMARY OF THE INVENTION

It is an object of the present invention to provide a device for anastomosing blood vessels and vascular prosthesis, either synthetic or biological with end-to-end or end-to-side configuration, in a way much easier with respect to the known techniques, that assure steadiness at least like that obtained with the technique of hand-sewn anastomosis.

The starting point of the present invention is the association of a outer containing device and an intra-prosthetic stent, that in combination contain as a sandwich the overlapping segments of anatomical ducts and a prosthesis, a segment of which is located in the duct, for example a vessel, that are being anastomosed to each other.

According to the invention, the outer containing device is formed by a stent of biocompatibile resilient material having memory effect, in a predetermined nominal position, suitable for enlarging elastically for engaging the outside of the duct, and returning to said nominal position, with containing function. This containing function has the object to prevent the diameter of the duct from increasing and without compressing the duct. The stent must have at least a length not less than half the outside diameter of the duct. In fact, it must be assured, for a sufficiently long duct portion, a steady and uniform grip of the wall of the duct to the prosthesis. The diameter in nominal position of the outer containing device, object of the present invention, is suitable for allowing the full expansion of the inner stent located in the prosthetic anastomosed segment with the anatomical duct.

Once the wall of the duct has been arranged between the outer stent and a prosthetic segment with expansible inner structure, the opposed resilient forces of the two elements are already capable of assuring a satisfactory connection between the duct and the prosthesis, much larger than that deriving from the single application of the stent graft, without that stitches are necessary for increasing the resistance of the anastomosis against leakage.

However, some separate stitches, for example two or three, can be applied for making axially integral to one another the outer stent, the wall of the duct, the prosthetic segment located in the duct and the relative expansible structure, to avoid any migration of the prosthesis. The addition of the stitches makes the anastomosis thus obtained much steadier axially at least comparably to a conventional hand-sewn anastomosis. More precisely, a line of stent knots more proximal to the prosthetic anastomosed segment are connected to the wall of the duct and to the outer stent.

Being the length of the containing device not less than half the diameter of the duct, around the possible stitches there is an enough wide area not subject to deformation, avoiding that the stitches concentrate the wall stresses, thus causing the prosthetic wall to tear or in any case to reduce the seal.

If the anatomical duct is a blood vessel, the presence of the outer containing device, or extra-vascular stent, assures a fixed and steady grip of the vessel wall segment to the prosthetic expansible segment, in opposition to the expanding action on the vessel wall segment caused both by the prosthesis and by the blood pressure on the prosthetic wall and maintains the vessel wall segment adherent to the prosthesis same.

Actually as observed after an endoluminal aortic aneurysm repair with stent-graft, the vessel wall segment being anastomosed, i.e. the proximal aortic neck, is subject to two forces that can cause its dilatation:
- a radial action from the inner metal expansible structure of the stent graft;
- the rhythmical blood pressure has also a radial direction; the blood column in fact presses between the meshes of the inner metal expansible structure of the stent graft, thus pressing radially through the prosthetic fabric on the vessel wall proximal neck, with expanding action with respect to the inner metal structure of the stent graft. Both actions then contribute to the dilatation of the vessel proximal neck, thus making the anastomosis less steady.

The extra-vascular stent according to the present invention is a device that is substantially different in its function from the extra-vascular containing devices commonly used, for limiting the dilatation of pathologically stenotic anatomical ducts once their lumen has been adjusted. In fact, the present device has containing action and, after solidarisation with single separate stitches with the intra-prosthetic stent, it stabilises the anastomosis.

According to a preferred embodiment, the extra-vascular stent object of the present invention has a longitudinal discontinuity that allows its opening for resilient divarication of the free ends for arranging it about a vessel to anastomose that has not been fully cut circumferentially.

This open stent can be made, in a not limitative embodiment, according to at least two forms:
- starting from a rectangular lamina of a chosen material worked in order to obtain a net or grid shaped central part and edges of increased thickness;
- a frame structure, folded into an arc up to approaching two opposite sides, with holes in which the free end engage of the net or grid shaped structure; after the connection of the net to the free sides of said frame structure a suitable device is obtained with the desired effects.

Alternatively, the extra-vascular stent is a circumferentially continuous sleeve, made of expansible or retractable meshes for achieving a desired diameter.

Preferably, the extra-vascular stent can be associated to a fabric arranged between the stent same and the external vessel wall.

According to another aspect of the present invention a device for making vascular by-pass comprises:
- the extra-vascular stent as above described, to be arranged at the vessel segment being anastomosed;
- a synthetic or biologic prosthesis, to be anastomosed with said vessel, having expansible structure;
- means for guiding a segment of the prosthesis to be anastomosed into the vessel segment and/or the extra-vascular stent about the vessel segment same.

In particular, according to a first embodiment of the invention, for end-to-end anastomosis the means for guiding the prosthesis into the vessel being anastomosed comprise:
- a first tubular guide, containing the prosthesis;
- a second tubular guide having an end suitable for entering the vessel proximal neck being anastomosed and for sliding on the first tubular guide, said second tubular guide being suitable for guiding the prosthesis in the vessel proximal neck being anastomosed.

The following may be also provided:
- a third tubular guide sliding on the second tubular guide and suitable for guiding the extra-vascular stent on the vessel proximal neck being anastomosed for releasing it on the proximal neck same, while said second tubular guide is still inserted into it; said third tubular guide being suitable for keeping the stent at a diameter larger than the vessel proximal neck being anastomosed.

Advantageously, the outer surface of said second guide and the inner surface of the third guide provide complementary sliding means engaging with each other. A mutual longitudinal sliding is thus allowed keeping in the meantime the inner surface of the third guide distanced from the external surface of the second guide, whereby the third guide can slide on the vessel proximal neck being anastomosed when the second guide has an end put into proximal neck same. The guide end at a predetermined distance from the end of the second guide, preferably to a distance from the edge of the second guide set between 1 and 2 cm.

The third guide can have gripping handles for allowing an its easy sliding of the second guide.

Once made the anastomosis, an easy removal of the guides is achieved in alternative by:
- the presence of longitudinal weakened lines for creating a longitudinal discontinuity and then a removal of the guide;
- a mechanism of "peel off", either "disposable" or "poly-use". In the latter case, for example, each guide can be made in two parts, with the free end conformed to allow a solid and reversible bayonet coupling.

The described method and application device of the prosthesis and of the extra-vascular stent are operable if a full cross section of the vessel wall segment being anastomosed has been made.

Instead, if the cross section of the vessel segment is partial, a extra-vascular open stent is necessary which can be fixed by means of divarication of its free end and then fitting it about the vessel segment same. In this case the presence of the third guide is not required and the device provides only the first and the second guide, the latter without the above described complementary sliding means. This latter way of anastomosing object of the present invention, has the advantage of being used for stabilizing the application to the aortic wall of stent graft previously located with endoluminal approach.

The application of the extra-vascular stent and of the separate stitches is carried out by means of visualisation of the position of the proximal meshes of the inner expansible structure of the stent graft, choosing the knots useful for solidarisation with the extra-vascular stent, by means of for example of Roentgen mapping as commonly used for application of stent grafts with endoluminal approach and relative follow-up.

Concerning the distal anastomosis, the location of the extra-vascular stent and the application, according to the above described technique, of single separate stitches, may be not necessary if the prosthetic segment with inner stent is put in for at least 10-15 mm in the corresponding vessel segment. In this case, for making the anastomosis described by the present invention the following are provided:
- a prosthesis having expansible structure to be put into the vessel segment being anastomosed;

means for guiding the prosthesis into the vessel segment being anastomosed.

In this case, the means for guiding the prosthesis into the vessel segment being anastomosed comprise preferably:
- a first tubular guide, containing the prosthesis;
- a second tubular guide having an end suitable for entering the vessel segment being anastomosed and sliding on the first tubular guide, the second tubular guide being suitable for guiding the prosthesis into the vessel segment being anastomosed.

Both the guides are structurally similar to those previously described and have the same mechanisms of removal, indicated for example and not limitative.

Advantageously, in the case of anastomosis with end-to-side configuration, a intra-vascular stent is provided comprising s tubular portion and an end portion that extends radially from an end of the tubular portion. The end portion is suitable for being put laterally into the main vessel to carry out an end-to-side anastomosis and is capable of collapsing elastically for allowing its passage in a side opening made in the wall main vessel.

Advantageously, the end portion has a plurality of elastic segments connected to it. Such segments radially extend in operative conditions and can be collapsed elastically for being put into a vessel being anastomosed. In particular, the segments are associated to a prosthetic material that covers the tubular portion and extends from it.

Each segment has been shown as rectangular only for example, not limitative. The prosthesis, which coats completely this cross section of the stent, eventually has the expanded shape like a "corolla".

The segments are opened, according to the invention, by means of two possible alternative mechanisms:

A first mechanism provides that the collapsed position is obtained forcing the segments to a position parallel to the axis of the tubular portion opposite with respect to the tubular portion same. When releasing the segments in the collapsed position, the segments move back owing to their memory and/or elastic effect, following a semi-circular movement up to approaching the prosthetic tubular portion. Within the vessel, however the vessel wall within which the anastomosis is made, limits the completion of the rotation, so that each element forces resiliently on the inner part of the vessel wall with which the anastomosis is made.

A second mechanism provides, instead, that the collapsed position is obtained forcing the elements to a position parallel to the axis of the tubular portion at the same of the tubular portion same. When releasing the segments in the collapsed position, the segments move forward owing to their memory and/or elastic effect, following a portion of circular trajectory in a direction opposite with respect to the tubular portion.

Preferably, for limiting an excessive opening of the segments beyond a radial position, at every resilient junction of the segments with the tubular portion an abutment is present.

A further alternative embodiment comprises, for the end portion, a ring structure with variable diameter connected with the tubular portion by means of a plurality of segments. Such segments lay in a plane orthogonal to the axis of the tubular portion and can rotate, driven by the variation of diameter of the ring, from a tangential position with respect to the tubular portion to a radial position. Therefore, the prosthetic material associated to the segments and to the ring pass from a collapsed to an extended position.

The variation of diameter of the ring structure can be obtained:
- for juxtaposition of the free end of the metal structure of the ring.
- for telescopic sliding of the ends with respect to each other, for deformation of the material of the ring structure.

According to this embodiment of the invention, a first tubular guide is provided suitable to force the tubular portion of the device at a predetermined diameter, as well as a second tubular guide is present, sliding on the first tubular guide, suitable for containing the end portion in a collapsed position, and to allow an extension to the radial position after its withdrawal sliding on the first tubular guide.

Also in this case, for an easy removal of the guides after the anastomosis, the following alternative solutions can be advantageously provided:
- the presence of longitudinal weakened lines for creating a longitudinal discontinuity and then a removal of the guide;
- a mechanism of "peel off", either "disposable" or "poly-use". In the latter case, for example, each guide can be made in two parts, with the free end conformed to allow a solid and reversible bayonet coupling.

Also in this type of anastomosis the application of extra-vascular stents is provided according to the invention, of the open type, arranged about the main vessel in a position respectively proximal and distal with respect to the prosthesis.

BRIEF DESCRIPTION OF THE DRAWINGS

Further characteristics and the advantages of the device for anastomosing blood vessels and vascular prosthesis (biological and not), according to the present invention, will be made clearer with the following description of an embodiment thereof with reference to attached drawings wherein:

FIG. 3 shows an exploded view of the device of FIG. 2;

Figure 1:
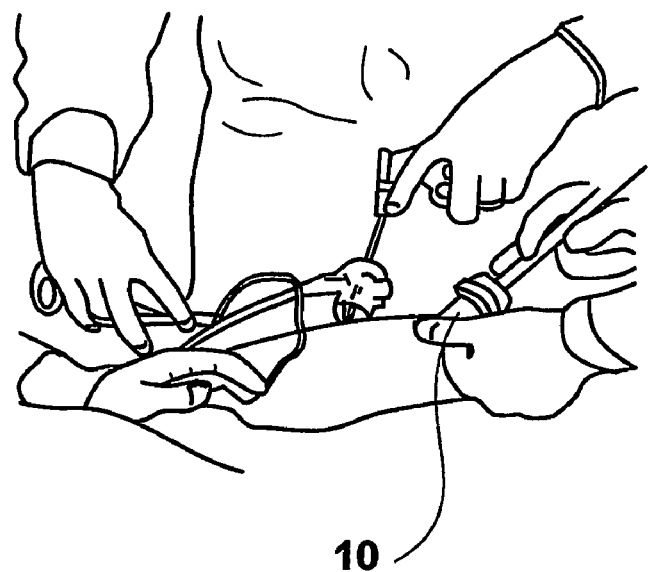
FIG. 1 shows a step of a surgery operation of application of a prosthesis at the abdominal aorta by laparoscopy using a device according to the invention.
Figure 13:
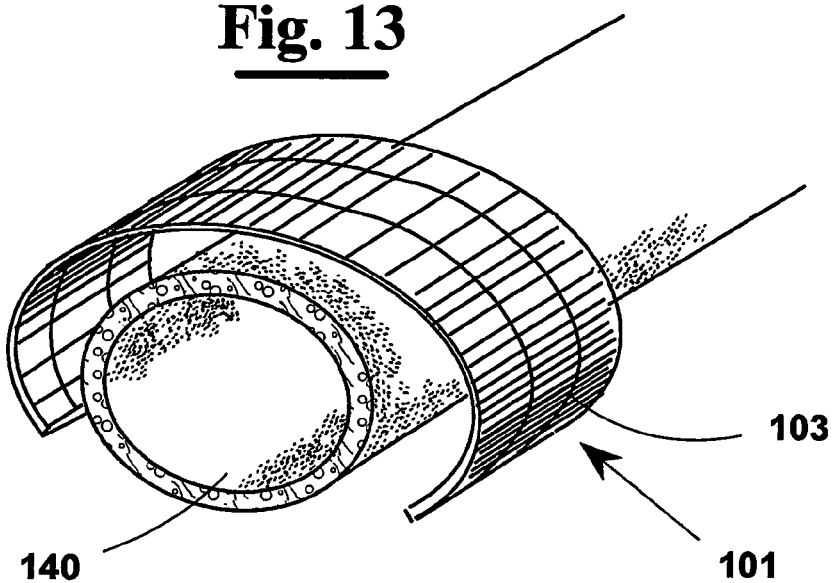
Figure 14:
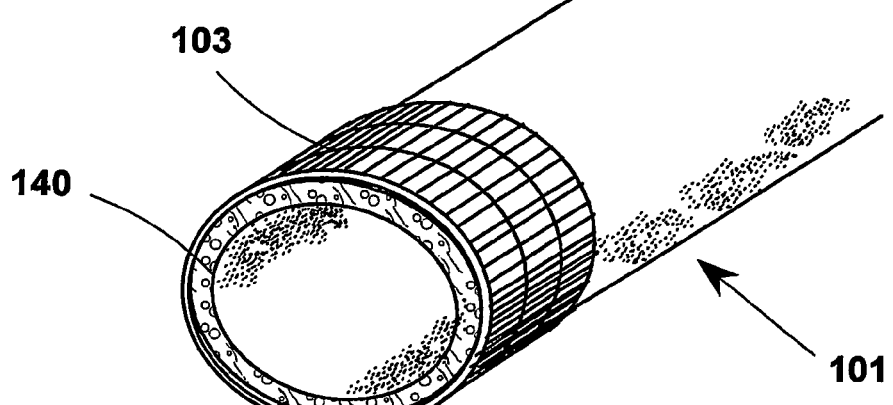
Figure 12:
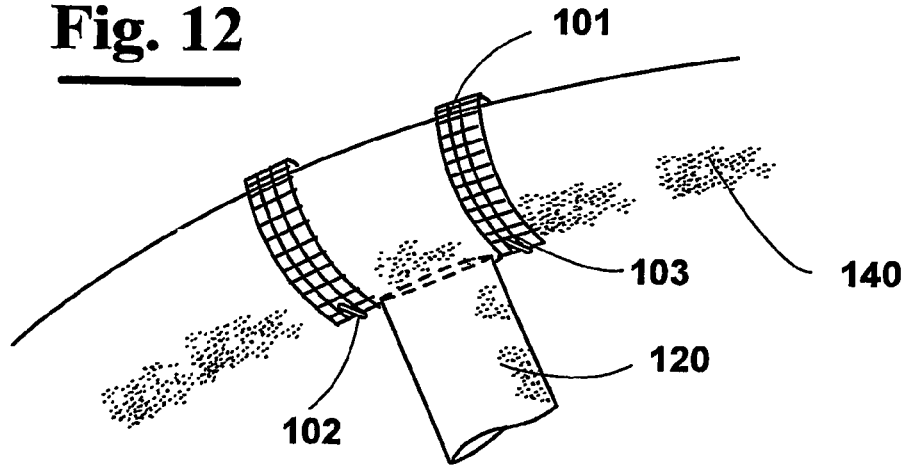
Figure 15:
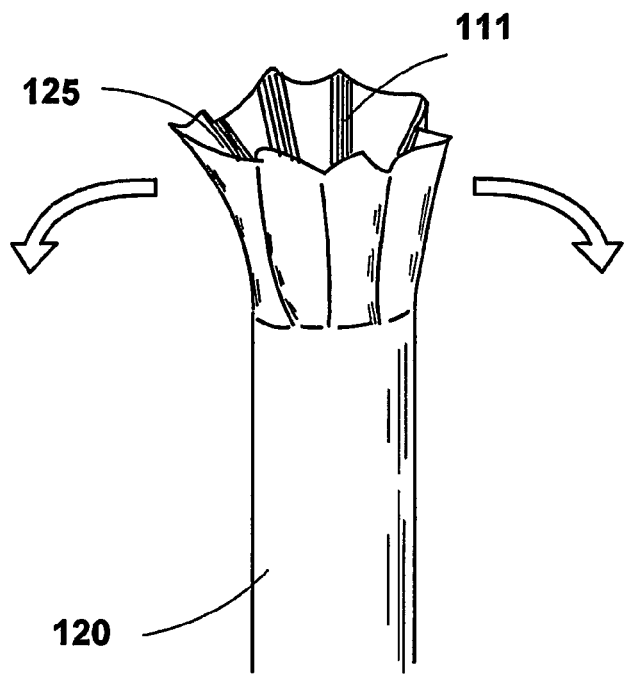
Figure 16:
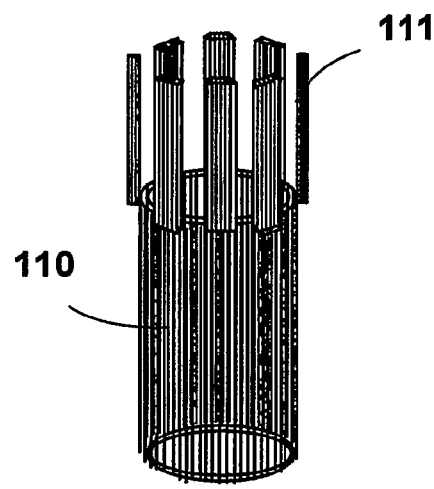
Figure 17:
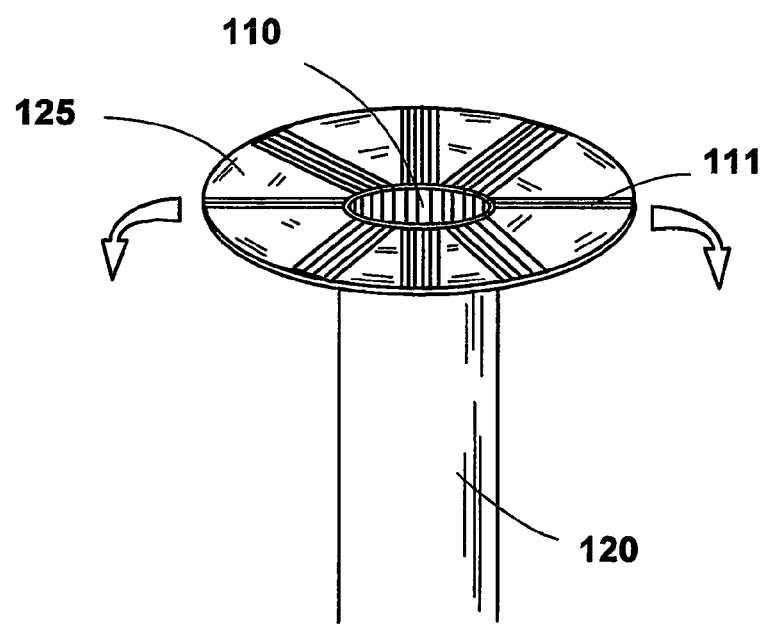
Figure 18:
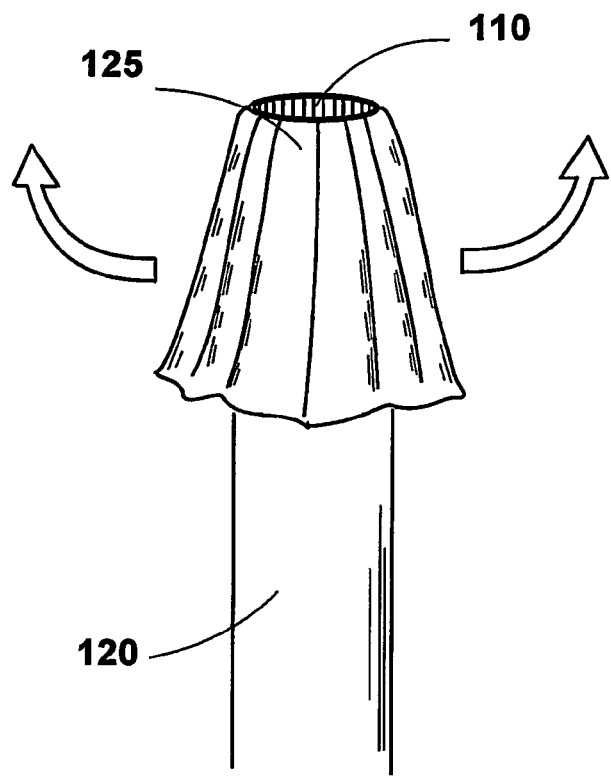
Figure 19:
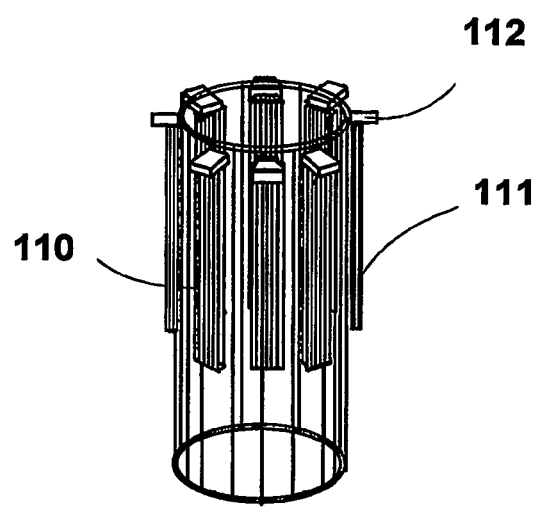
Figure 20:
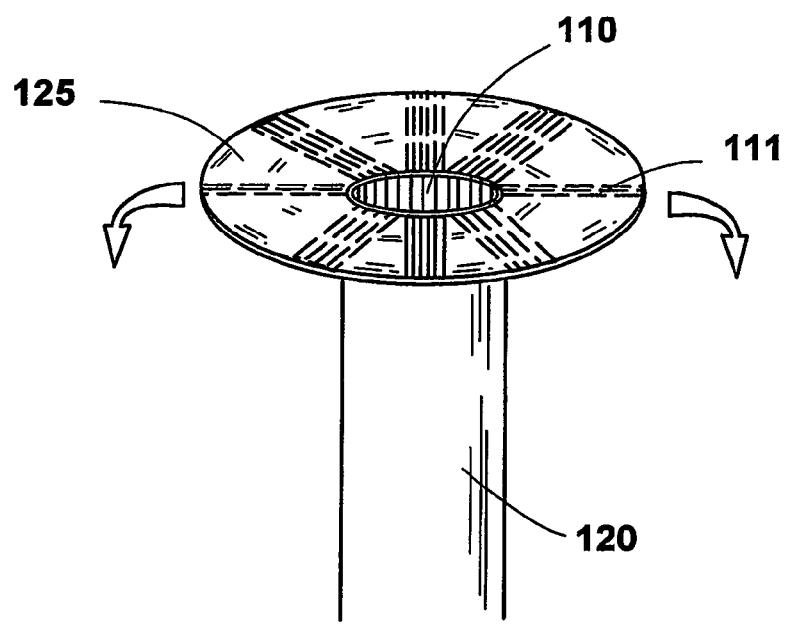
Figure 21:
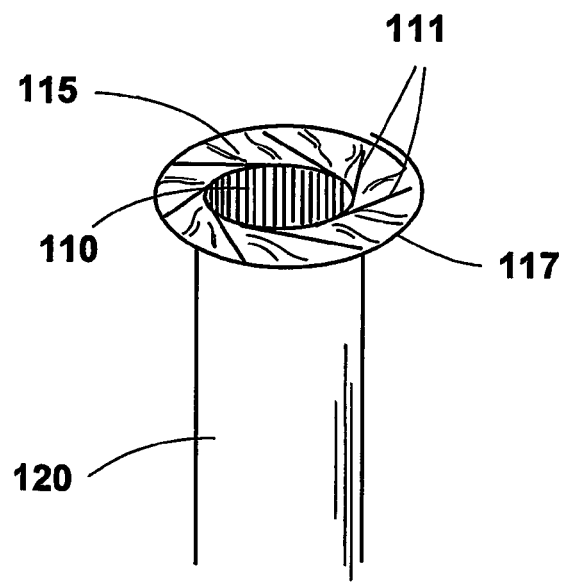
Figure 22:
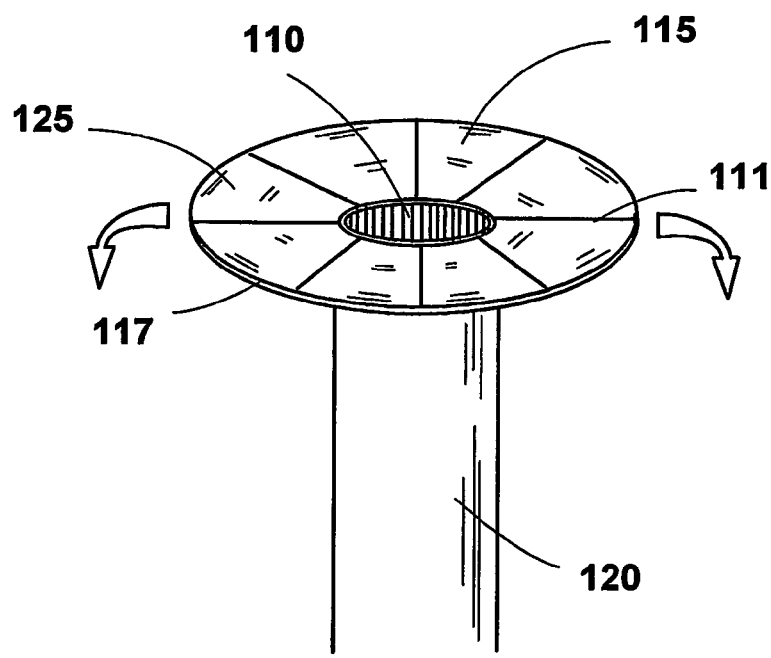
Figure 26:
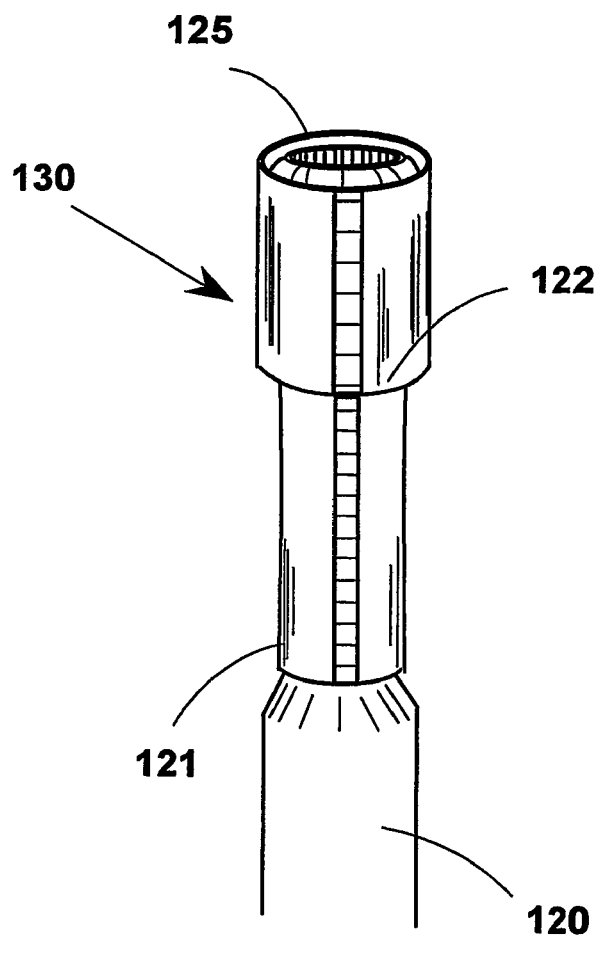
Figure 28:
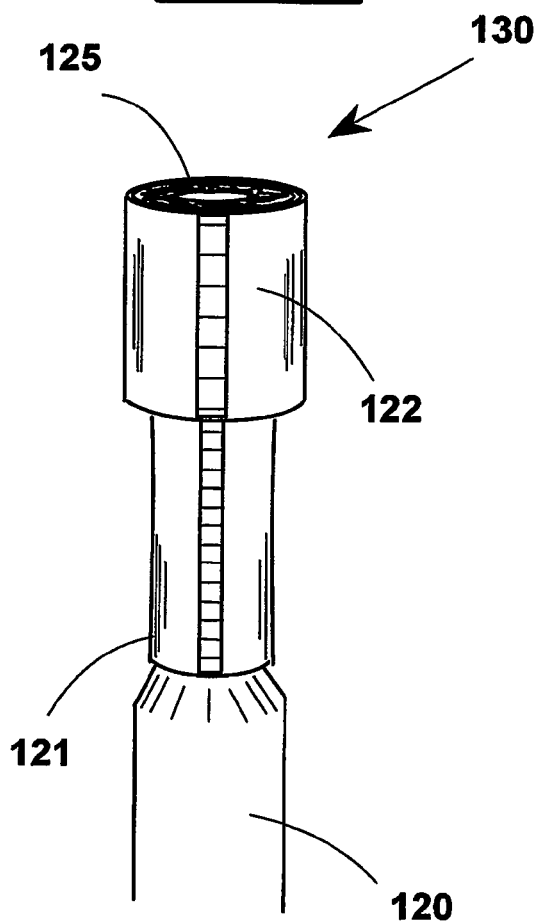
Figure 33:
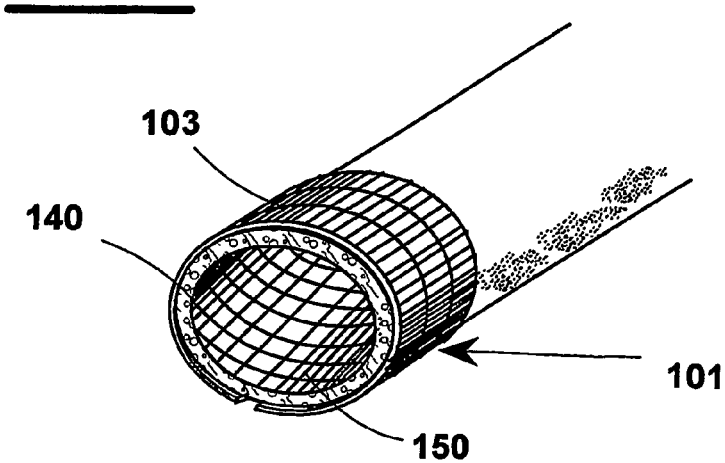

figure from 3A to 3C show three steps of assembling the device of FIG. 1;

figures from 4 to 9 show six steps of application of a prosthesis having expansible structure by the device of FIG. 1;

FIGS. 10 and 11 show a preferred embodiment of the device of FIG. 1, with a longitudinal discontinuity for opening, at the end of the introduction, the tubular guides of the device;

FIG. 12 shows a perspective view of an extra-vascular stent, according to the invention, in the open configuration with respect to a vessel being anastomosed;

FIG. 13 shows the extra-vascular stent of FIG. 13, in the configuration "closed" on the vessel;

FIG. 14 shows diagrammatically an end-to-side anastomosis between a blood vessel and a vascular prosthesis, made by the device of the present invention;

FIG. 15 shows an elevational side view of a first type of vascular prosthesis;

FIG. 16 shows diagrammatically a intra-prosthetic stent for the vascular prosthesis of FIG. 15;

FIG. 17 shows the prosthesis-stent device of FIGS. 15 and 16 in operative conditions;

FIG. 18 shows an elevational side view of a second type of vascular prosthesis, according to the invention;

FIG. 19 shows diagrammatically a intra-prosthetic stent for vascular prosthesis of FIG. 18;

FIG. 20 shows the prosthesis-stent device of FIGS. 18 and 19 in operative conditions;

FIG. 21 shows a third type of intra-prosthetic stent;

FIG. 22 shows the prosthesis-stent device of FIG. 21 in operative conditions;

figures from 23 to 28 show respectively three types of prosthesis like FIGS. 15-22 with use of guides for the introduction in a blood vessel being anastomosed;

figures from 29 to 32 show in turn the steps of introduction and of application of the prosthesis-stent device with guides according to FIGS. 24, 26 and 28 to the vessel being anastomosed for making the end-to-side anastomosis of FIG. 12;

FIG. 33 shows diagrammatically the device of FIGS. 12 and 13 used for making a intra-vascular prosthesis integral to a vessel;

figures from 34 to the 37 show a perspective view of three alternative embodiments of the extra-vascular stent of FIG. 33;

FIG. 38 shows an extra-vascular stent net-like having protruding portions of wire for connection to the frame of FIG. 37.

DESCRIPTION OF A PREFERRED EMBODIMENT

In figures from 1 to 38 some possible embodiments are described of a outer containing device for making an end-to-end or end-to-side anastomosis between an anatomical duct and a prosthesis, according to the present invention.

The device can be used, in its different embodiments, in open surgery operations of traditional type, or also of laparoscopic type, as shown for example in FIG. 1, where the device is indicated with 10.

Figure 2:
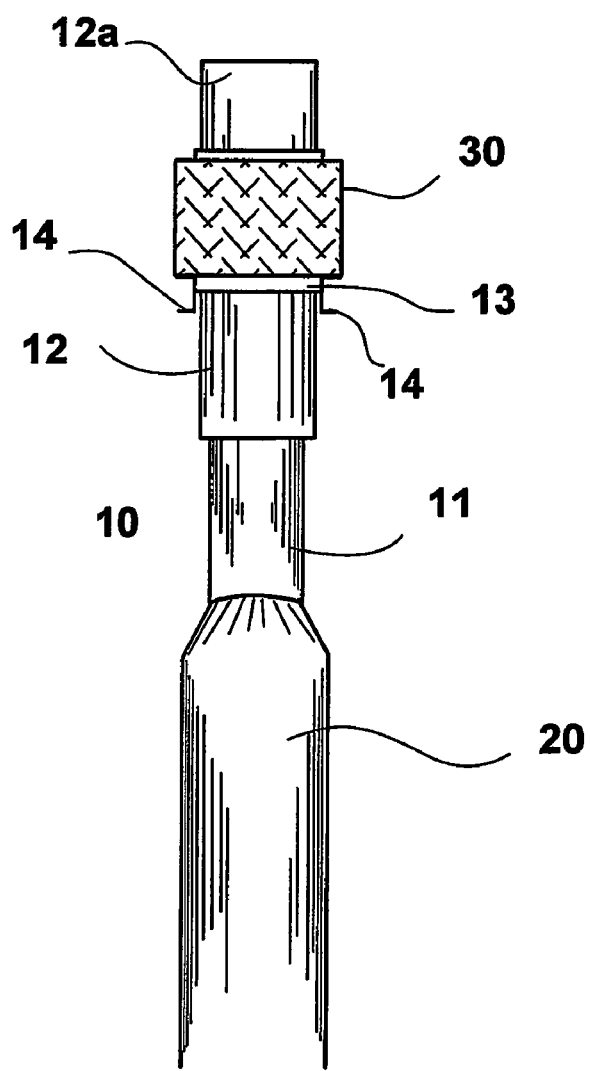
FIG. 2 shows a longitudinal view of a device according to the invention for application of a vascular prosthesis.

The device 10, FIGS. 2 and 3, comprises three tubular guides 11, 12 and 13, and, in the case of an end-to-end anastomosis, it connects:

a prosthesis 20, of auto expansible type for all or part of its length, having an end 20a to put in the proximal neck of a vessel being anastomosed;

an extra-vascular stent 30, according to the invention, to be arranged on the proximal neck, able to adapt at a diameter equal to the proximal neck same.

The device 10 has then the object to guide the intra-vascular prosthesis 20 into the proximal aortic neck and the extra-vascular stent 30 about the proximal neck, in the following way:

the first tubular guide 11 contains the prosthesis 20 (FIG. 3A) that is kept at a diameter less than the proximal neck;

second tubular guide 12, having an end 12a suitable for entering the proximal neck and for guiding the prosthesis 20 into the proximal neck same, slidingly engages on the first tubular guide 11 (FIG. 3B);

the third tubular guide 13 slidingly engages on the second tubular guide 12 (FIG. 3C) and keeps the extra-vascular stent 30 at a diameter larger than the proximal neck, for eventually releasing the extra-vascular stent 30 on the proximal neck same while said second tubular guide 12 is still inserted into the latter.

Figure 6:
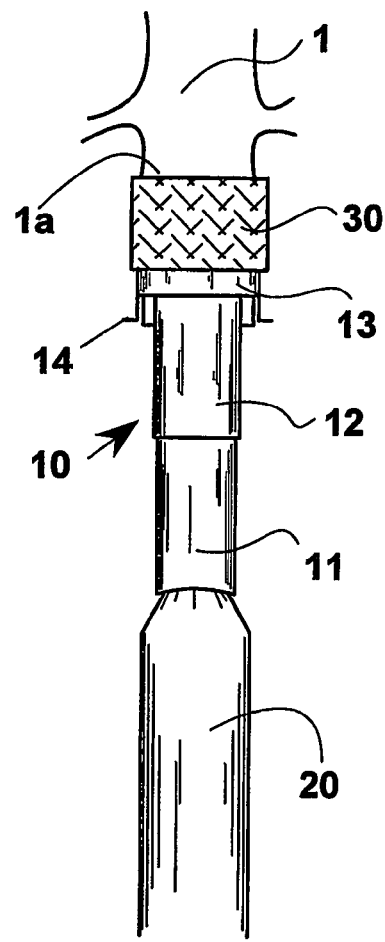
Figure 7:
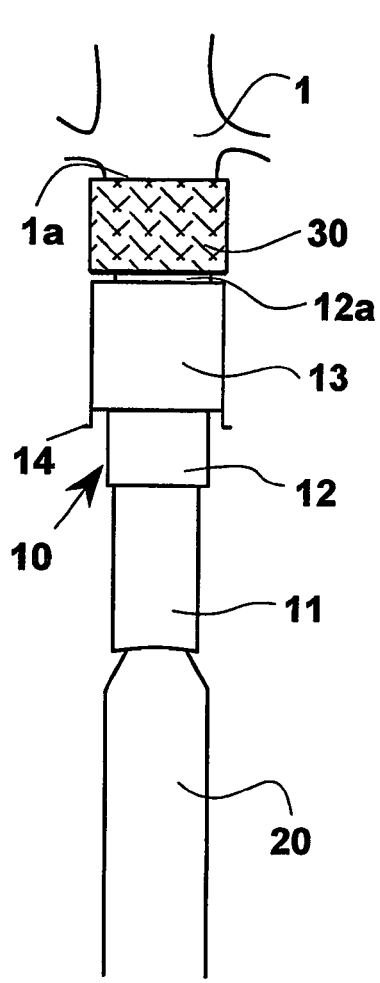
Figure 8:
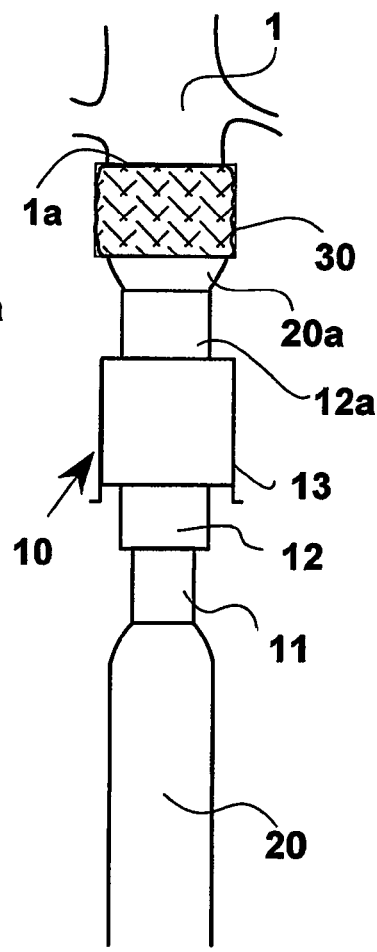

In more detail, with reference to figures from 4 to 9, the device 10 ready for operation is presented before the proximal aortic neck 1a for carrying out the anastomosis (FIG. 4), with the following steps:

introduction (FIG. 5) of the prosthetic device 10 into the proximal aortic neck 1a, with penetration of the end 12a of the second tubular guide 12; the proximal aortic neck locates between the second and the third tubular guide respectively 12 and 13, even with a certain play;

juxtaposition (FIG. 6) of third guide 13 on the proximal aortic neck 1a up to reaching at the end 12a of second guide 12;

withdrawal (FIG. 7) of third guide 13 with release of the extra-vascular stent 30 on the proximal aortic neck 1a; this step is carried out with the aid of an instrument that keeps still the extra-vascular stent 30 with respect to the third guide 13, which is withdrawn by handles 14;

sliding movement (FIG. 8) of the second guide 12, moving away from the vessel 1 being anastomosed, in order to allow full auto-expansion of the end 20a of the prosthesis 20 within vessel 1; more precisely, auto expansible portion 20a passes from the compressed position of FIG. 3a in the end 12a of second guide 12 (FIG. 3A) to the expanded position of FIG. 3, with direct contact with the inner wall of the proximal neck (FIG. 8);

opening and removing (FIG. 9) in turn the three guides 11, 12 and 13 cutting along the weakened lines 11b, 12b and 13b (FIGS. 10 and 11).

Once located the prosthesis 20 into the proximal neck and the extra-vascular stent 30 onto the proximal neck same, the opposed resilient forces of the two elements 20 and 30 are already capable of assuring a satisfactory connection.

The application of some stitches, for example two or three, cause the anastomosis to be steady and resistant at least comparably to a hand-sewn anastomosis.

The length of the containing device 30 is preferably not less than half the diameter of the proximal aortic neck 1a. Since the aortic diameter is about 2-3 cm, the height of the stent can be for example 1.5-2 cm. This way around the possible stitches an enough wide area is present not subject to deformation, avoiding that the stitches concentrate the wall stresses, thus causing the prosthetic wall to tear or in any case to reduce the seal.

In the experiments carried out for testing a vascular anastomosis the proximal aorto—prosthetic anastomosis has been chosen. An anastomosis obtained with manual traditional running suture has been assumed as gold standard. Ex-vivo tests have been performed on bovine and porcine aortic segments. Each test compared the new type of anastomosis to an hand-sewn anastomosis, both carried out on segments obtained dividing a single aortic specimen. Every test entailed aortic segments were similar regarding to inner diameter and parietal thickness. Assignment of aortic segments has been, randomly determined. Hand-sewn anastomoses have been carried out with Prolenee® 3-0 and Dacron® prostheses. For making this new anastomosis the following procedure has been used:

1. arrangement of extra-vascular stent on the proximal aortic neck; the stent being chosen with diameter as described above and with distal edge coinciding with that of the proximal aortic neck;
2. arrangement of the stent graft in the proximal aortic neck for 10-15 mm (depending on the structure of the stent graft used; stent grafts commonly available on the market have been used);
3. application of separate stitches of polypropylene 3-0 (PROLENE®), in order to make the stent, the aortic wall and the stent graft integral to one another; each stitch connected the aortic wall and the extra-vascular stent around the knots of the meshes most proximal to the metal inner armature of the stent graft used.

After making the two types of anastomosis, every aortic segment—prosthesis union has been verified, concerning its resistance to a force directed according to a main axis; the free end of the aortic segment has been connected to a special support so that the aortic segment prosthesis union is perpendicular to the ground, while to the free end of the prosthesis a force at first of 0.25 Newton has been applied and progressively increased with 0.25 Newton steps.

In all the stretched unions laceration of the aortic wall occurred proximally to the anastomosis with the prosthesis; the characteristics of the break of the aortic wall are macroscopically similar in all the experiments independently from the type of anastomosis: the causer of the break always were the resistance of the aortic wall and not of the anastomosis. The similarity of the results obtained, as indicated below

|  | hand-sewn anastomosis | new anastomosis |
|---|---|---|
| porcine specimen, Newton at the breaking point | 21.58 ± 1.6 | 24.03 ± 1.4 |
| bovine specimen, Newton at the breaking point | 53.95 ± 2.0 | 54.6 ± 1.2 | show a resistance of the anastomosis made with the method alike to that traditional, presently considered as gold standard.

If is not possible to cut the aorta circumferentially, but only to cut it partially, it is impossible to apply a cylindrical shaped extra-vascular stent at the anastomosis. Therefore, in this case, always according to the invention, the extra-vascular stent has a cylindrical shape with a longitudinal discontinuity that allows its location about the aorta (FIGS. 12 and 13).

Even with the type of extra-vascular stent of FIGS. 12 and 13 the same guiding means of the prosthesis can be used as above indicated and shown in figures from 2 to 9. Alternatively, if the surgeon applies the stent of FIGS. 12 and 13 with other systems, the means for introducing can be simpler, for example shown in the only FIG. 3A, being the third guide not necessary any more.

The characteristics of the open extra-vascular stent, according to FIGS. 12 and 13, both analysed with a special mathematical model and verified experimentally, allow:

the divarication capability, even repeated more times sequentially, of the free ends up to overcome its inner diameter, with relatively weak forces; this aspect allows easy location about the vessel proximal neck with to anastomose;

resistance to pressure acting in a radial direction up to 280-300 mmHg, without structural alterations and with maximum increase of the inner diameter of 1 mm; this characteristic allows the containing and not constrictive action of the extra-vascular stent object of the present invention; in fact once it has been located about the vessel proximal neck the free ends do not tend at all to approach further, being the whole device designed for opposing to a divarication owing to radial expansion on the inner surface, as practically is the expansion of a artery vessel owing to blood pressure. In the experiments under the present invention this device has been made of Nitinol.

An alternative embodiment of the invention, for making an end-to-side anastomosis, is described with reference to figures from 14 to 34.

In particular, with reference to FIG. 14, an end-to-side anastomosis (or bypass) between a blood vessel 140, for example the aorta, and a prosthesis 120 can be made by extra-vascular stents 101 and a application device described hereinafter.

More precisely stent 101 of extra-vascular type, according to the present invention, is located about the vessel 140 near the anastomosis same with application of stitches 102. Each extra-vascular stent 101 has a cylindrical shape with a longitudinal discontinuity that allows its location about the vessel 140 with "handcuffs" like mechanism (FIGS. 12 and 13).

The diameter of each extra-vascular stent 101 is chosen in order to adapt to that of the vessel for a containing and not compressive function, owing to the structure of the stent here not described in detail, with the so called "memory effect", owing to the presence of circumferential elements 103 of biocompatibile resilient material (FIGS. 12, 13 and 14).

Figures from 15 to 22 show three different embodiments of a intra-prosthetic stent 110, according to the invention, located within the prosthesis 120 being anastomosed, made of fabric or suitable biocompatible flexible or biologic material. Stent 110 (FIGS. 16 and 19) is made of two parts: a tubular part, which has a structure similar to that of the commonly used stents of auto expansible type, and an end part, which allows an end-to-side anastomosis, by means of segments 111 that in the final position are arranged radially with respect to the axis of the stent 110.

The "corolla" like opening of segments 111 is obtained according to the invention, by means of two mechanisms alternative to each other.

In FIGS. 15, 16 and 17 a first embodiment is shown, according to which segments 111 are elastically connected to stent 110 so that, starting from a forced position parallel to the axis of the stent 110 (FIG. 16), and extending beyond its end, tend to achieve (arrows of FIG. 15) a radial position (FIG. 17) and to go further it. Therefore, the proximal portion 125 of the prosthesis 120 fitting segments 111 passes from a collapsed position (FIG. 15) to a circular shape (FIG. 17).

As shown by the arrows of FIG. 17, the segments 111 maintain a resilient force pushing gently against the inner walls of the vessel. In FIGS. 18, 19 and 20 a second different embodiment is shown of the invention for stent 110, wherein segments 111, starting in forced condition, parallel to the axis of stent 110 and adjacent to its side surface, tend to move radially (FIG. 20). For limiting an excessive opening of segments 111, at every resilient junction with the proximal end of stent 110, an abutment 112 can be present. As shown by the arrows of FIG. 20, segments 111 maintain a resilient force for pushing gently against the inner walls of the vessel.

A third embodiment provides at the end portion of the stent 110 a ring structure 117 (FIG. 21), made of biocompatibile material, capable of adjusting its diameter elastically with memory effect mechanism of the material same. This ring structure 117 is connected with the proximal end of stent 110 and with prosthesis 120 by means of segments 111 structurally integrated with stent 110 same.

Segments 111 lay in a plane orthogonal to the main axis of stent 110 and can rotate from a tangential position with respect to stent 110 (FIG. 21) to a radial position. This rotation is driven by the variation of diameter of ring 117. The fabric 115 of the prosthesis passes from a collapsed position (FIG. 21) to an extended condition (FIG. 22) following segments 111. As shown by the arrows of FIG. 22, the segments 111 maintain a resilient force pushing gently against the inner walls of the vessel.

Figure 25:
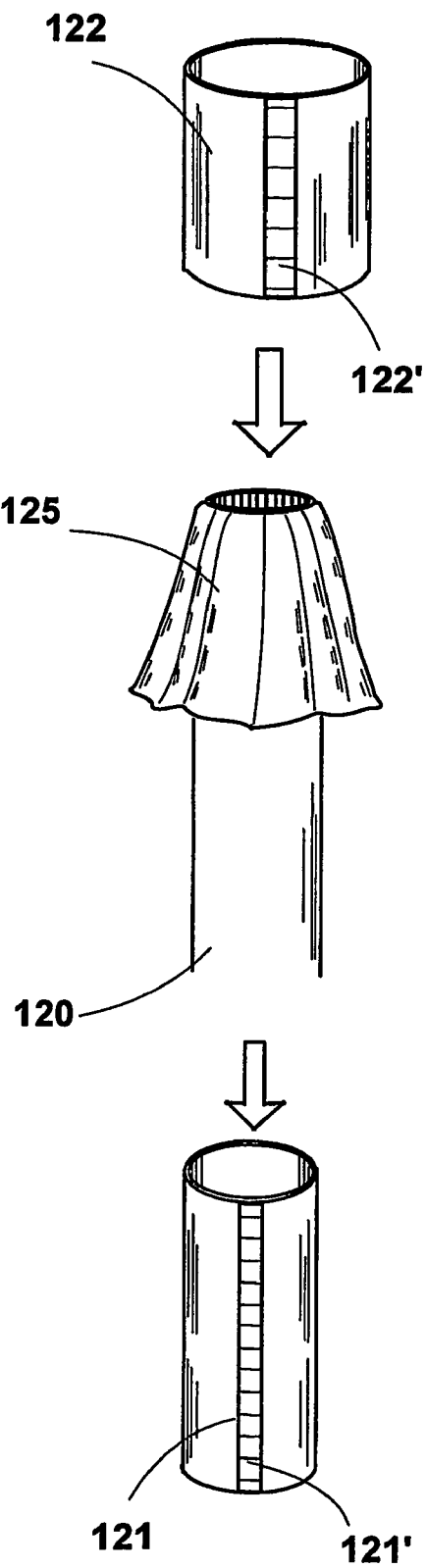
Figure 27:
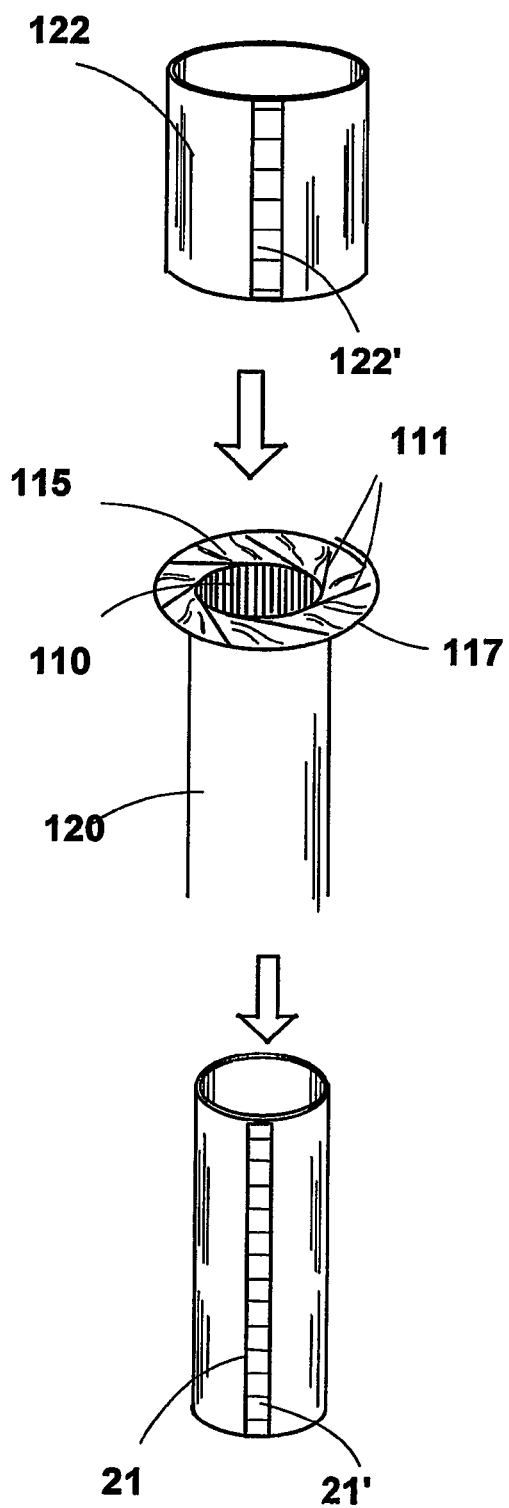
Figure 29:
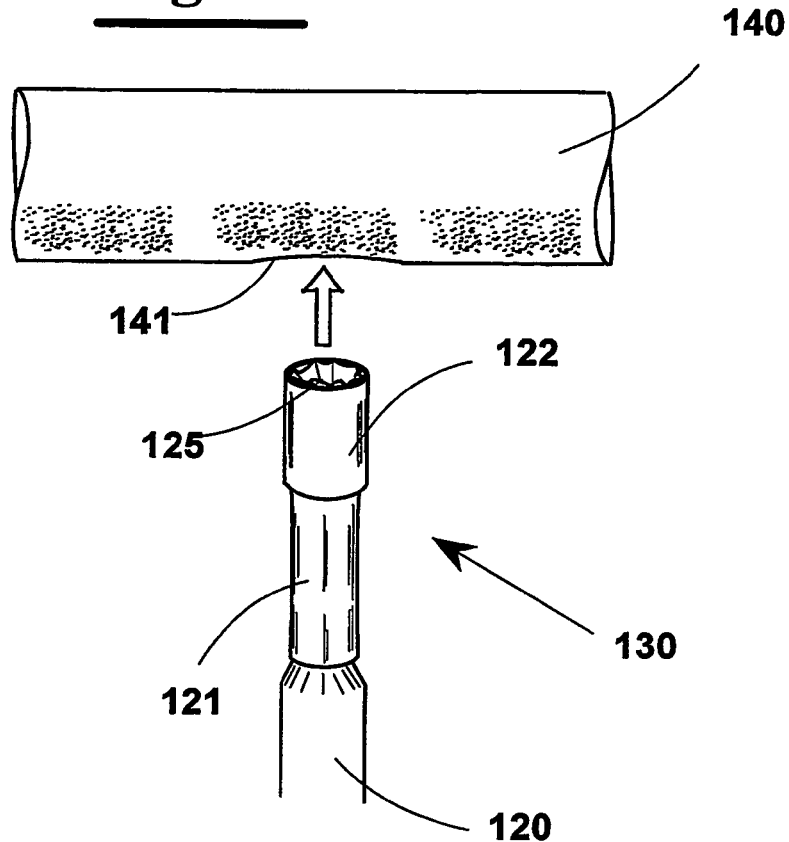
Figure 30:
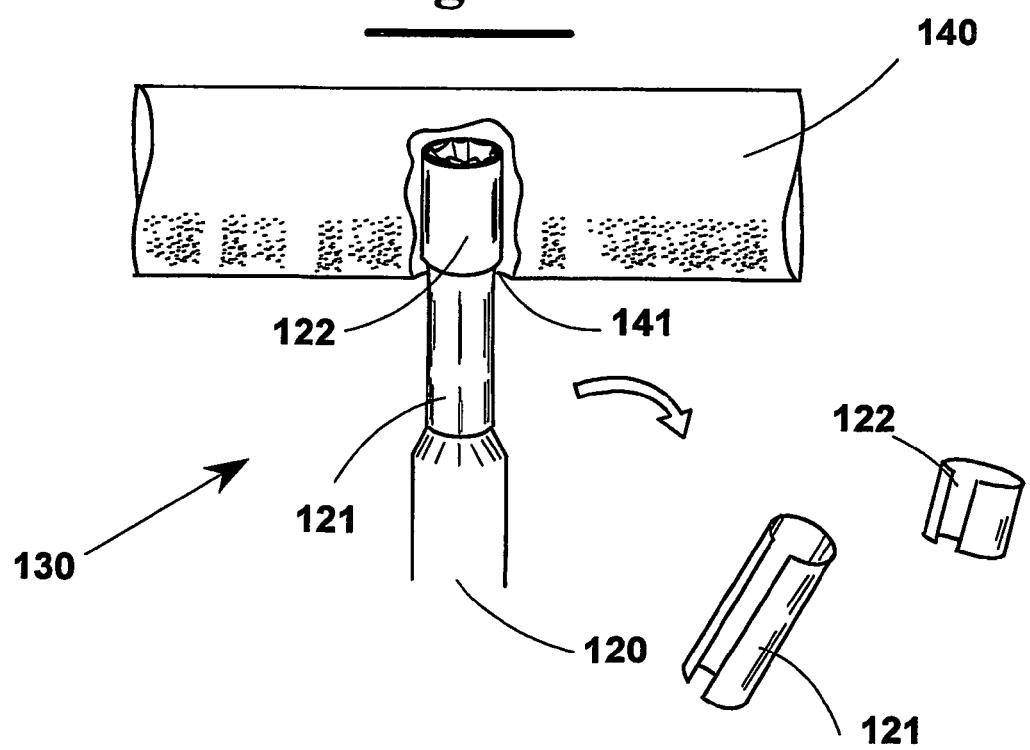
Figure 31:
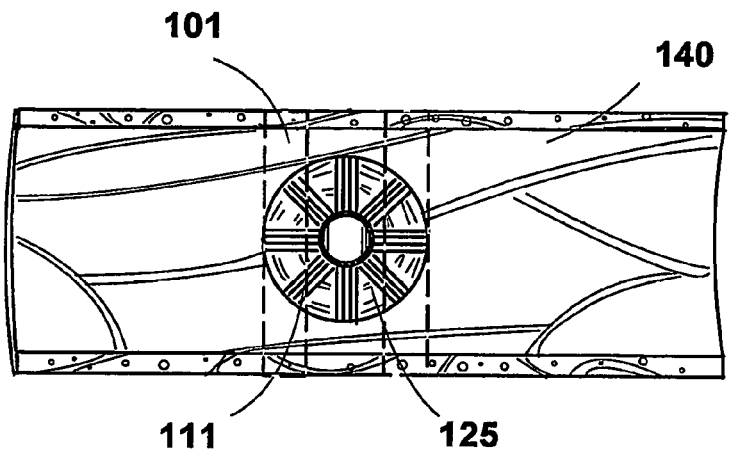

For positioning each intra-prosthetic stent 110 (FIGS. 15, 18 and 21) and prosthesis 120 to it connected in the vessel 140 being anastomosed, the use is provided of:

a first tubular guide 121 containing the linear portion of the stent 110-prosthesis 120 structure, substantially for reducing its of diameter (FIGS. 23, 25 and 27);

a second tubular guide 122, sliding on the first tubular guide 121, which covers it, containing end portion of stent 110 with segments 111 collapsed inside and a contiguous part of first guide 121 same; the free end of second guide 122 is suitable for entering the arterioctomy 141 (FIGS. 29 and 30) of the vessel 140 at which the anastomosis must be made, guiding in part the first guide 121 for bringing in part the prosthesis 120 into the vessel 140.

The device 130 of the invention, ready for making the end-to-side anastomosis, is therefore shown in FIGS. 24, 26 and 28, formed by prosthesis 120 with intra-prosthetic stent 110 in the two guides 121 and 122.

In figures from 29 to 32 the different steps are diagrammatically shown, according to the present invention, for making an end-to-side anastomosis.

After having clamped and cut at 141 the wall of the vessel 140 to anastomose, device 130 is introduced into the cut 141, according to the invention, from the side of the free end of second guide 122.

Then, guide 122 slides on the guide 121 allowing collapsed ends 111 of intra-prosthetic stent 110 to be released.

In the case of device 130 of FIG. 26, a further movement is necessary of stent 110 in vessel 140 and, after the release of end 111, all the device is withdrawn in a distal direction to assure the juxtaposition of the intra-vascular end of the stent 110 onto the vessel wall 140. Then, the second and the first guide (122 and 121) are removed in turn which, for making easier the opening in longitudinal direction, comprise weakened portions 121' and 122'. Alternatively guides 121 and 122 can be made in two or more releasable parts.

After a correct location of elements 111, the opposed resilient forces of stents 110 are already capable of assuring a satisfactory vessel-prosthetic connection, both for widening due to the removal of first guide 121 and for opening end portion 111 after removal of second guide 122. The elasticity shown by the arrows of FIGS. 17, 20 and 22 makes easier the adhesion of end portion 111 to vessel 140.

Figure 32:
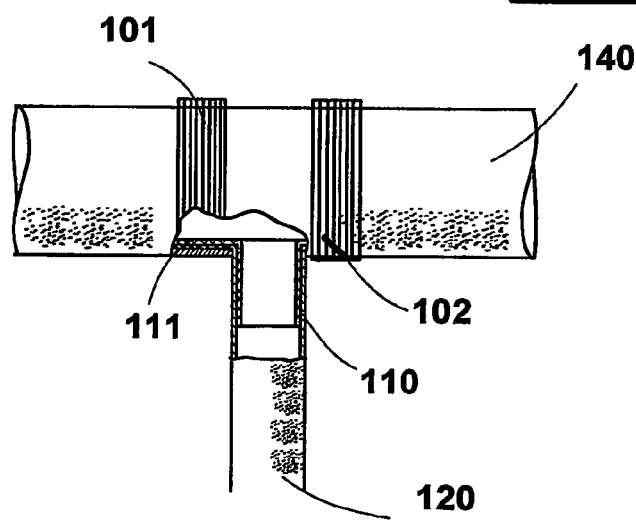

For a steady and much more resistant anastomosis, extra-vascular stents 111 (FIG. 32) can be applied with the addition of some separate single stitches 102, located in order make integral each extra-vascular stent 101, the vessel wall 140 and the end portion 111 that extends from the prosthesis 120 (FIG. 32) to one another.

In particular, each point 102 is fixed to the vessel wall 140 with which the anastomosis is achieved at the knots corresponding of the meshes of the extra-vascular stents 101 of end portion 111.

FIG. 33 shows as the extra-vascular stent 101 of FIGS. 12 and 13, with reticular structure, have circumferential resilient stiffening elements, capable of giving a resilient memory to all the stent, used for making a intra-vascular prosthesis 150 integral to a vessel 140. For example, this can be carried out for making aorta integral to the portion proximal of a stent graft located with intra-vascular methodologies.

In FIGS. 34 and 35 alternative embodiments are shown of this extra-vascular stent 101 with "open" configuration. According to this embodiment, stent 101 is a rectangular lamina 201 or 201' of a chosen material, worked in order, to obtain a central part 203 structured like a net or grid. For an increased resilient response and at the same time lightness of the structure, the central part 203 can be of minimal thickness with respect to the edges.

Alternatively, as shown in FIG. 36, a possible embodiment of the stent 401 is obtained by crossing longitudinal elements 402 and ring elements 403 to one another other, in order to provide a light structure with high void rate.

In a further alternative embodiment, the stent can comprise a frame 301 folded into an arc with longitudinal opposite approaching elements 302. In particular, the frame 301 can be associated to a structure 401' (FIG. 38) similar to that of FIG. 36, but provided with free ends 404 engage into holes 305 made on frame 301 same, obtaining a device, not shown, suitable to fulfil the requirements.

The foregoing description of a specific embodiment will so fully reveal the invention according to the conceptual point of view, so that others, by applying current knowledge, will be able to modify and/or adapt for various applications such an embodiment without further research and without parting from the invention, and it is therefore to be understood that such adaptations and modifications will have to be considered as equivalent to the specific embodiment. The means and the materials to realise the different functions described herein could have a different nature without, for this reason, departing from the field of the invention. It is to be understood that the phraseology or terminology employed herein is for the purpose of description and not of limitation.

What is claimed is:

1. A method for anastomosing an anatomical duct with a vascular prosthesis comprising the steps of:
arranging said vascular prosthesis within the anatomical duct
providing an outer containing element of biocompatibile resilient material having a memory effect;
elastically enlarging the outer containing element from a predetermined nominal shape to an enlarged shape;
arranging the outer containing element outside the anatomical duct;
returning said outer containing element to said nominal shape such that the anatomical duct is sandwiched between the outer containing element and the vascular prosthesis, wherein the nominal shape of the outer containing element is shaped to prevent the diameter of the duct from increasing, without compressing the duct, and wherein said outer containing element has length not less than half the outside diameter of the anatomical duct.

2. The method, according to claim 1, wherein said outer containing element has a longitudinal discontinuity that allows divarication of its free end at the ends for engaging said anatomical duct.

3. The method, according to claim 2, made starting from a rectangular lamina worked in order to obtain a central part of the lamina that is structured like a net or grid.

4. The method for anastomosing an anatomical duct and a vascular prosthesis, according to claim 2, wherein said outer containing element has circumferential elements in a biocompatibile resilient material having memory effect with possibility of extending elastically up to engaging the duct and returning to a containing shape.

5. The method for anastomosing an anatomical duct and a vascular prosthesis, according to claim 2, wherein said outer containing element is a rectangular lamina folded into an arc.

6. The method for anastomosing an anatomical duct and a vascular prosthesis, according to claim 5, wherein said rectangular lamina has a plurality of through holes.

7. The method for anastomosing an anatomical duct and a vascular prosthesis, according to claim 6, wherein said through holes are circular.

8. The method for anastomosing an anatomical duct and a vascular prosthesis, according to claim 6, wherein said through holes are polygonal.

9. The method, according to claim 1, wherein said outer containing element is a sleeve having meshes expansible or retractable for achieving a desired diameter.

* * * * *